(12) United States Patent
Cosman

(10) Patent No.: US 6,241,725 B1
(45) Date of Patent: *Jun. 5, 2001

(54) HIGH FREQUENCY THERMAL ABLATION OF CANCEROUS TUMORS AND FUNCTIONAL TARGETS WITH IMAGE DATA ASSISTANCE

(75) Inventor: Eric R. Cosman, Belmont, MA (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/661,802

(22) Filed: Jun. 11, 1996

Related U.S. Application Data

(63) Continuation of application No. 08/167,676, filed on Dec. 15, 1993, now abandoned.

(51) Int. Cl.[7] ................................................. A61B 17/39
(52) U.S. Cl. ................................. 606/41; 606/49; 600/41; 600/439; 607/99
(58) Field of Search ................................. 606/41, 43, 49; 607/99, 101, 102, 113; 128/653.2, 660.03; 600/439, 411

(56) References Cited

U.S. PATENT DOCUMENTS

| 4,608,977 | * | 9/1986 | Braun ................................ 606/130 |
| 4,662,368 | * | 5/1987 | Hussein et al. ..................... 607/113 |
| 4,848,196 | * | 7/1989 | Wiksell et al. ...................... 607/99 |
| 4,907,589 | * | 3/1990 | Cosman .............................. 606/41 |
| 5,099,846 | * | 3/1992 | Hardy ................................. 128/653.2 |
| 5,197,466 | * | 3/1993 | Morchosky et al. ................. 607/113 |
| 5,284,144 | * | 2/1994 | Delannoy et al. ................... 128/653.2 |
| 5,323,778 | * | 6/1994 | Kandarpo et al. ................... 607/101 |
| 5,323,779 | * | 6/1994 | Hardy et al. ........................ 178/653.7 |
| 5,383,876 | * | 1/1995 | Nardella ............................. 606/49 |
| 5,403,311 | * | 4/1995 | Abele ................................. 606/49 |
| 5,458,597 | * | 10/1995 | Edwards et al. ..................... 606/41 |

FOREIGN PATENT DOCUMENTS

2242132 * 9/1991 (GB) .

* cited by examiner

Primary Examiner—Lee Cohen

(57) ABSTRACT

This invention relates to the destruction of pathological volumes or target structures such as cancerous tumors or aberrant functional target tissue volumes by direct thermal destruction. In the case of a tumor, the destruction is implemented in one embodiment of the invention by percutaneous insertion of one or more radiofrequency probes into the tumor and raising the temperature of the tumor volume by connection of these probes to a radiofrequency generator outside of the body so that the isotherm of tissue destruction enshrouds the tumor. The ablation isotherm may be predetermined and graded by proper choice of electrode geometry and radiofrequency (rf) power applied to the electrode with or without temperature monitoring of the ablation process. Preplanning of the rf electrode insertion can be done by imaging of the tumor by various imaging modalities and selecting the appropriate electrode tip size and temperature to satisfactorily destroy the tumor volume. Computation of the correct three-dimensional position of the electrode may be done as part of the method, and the planning and control of the process may be done using graphic displays of the imaging data and the rf ablation parameters. Specific electrode geometries with adjustable tip lengths are included in the invention to optimize the electrodes to the predetermined image tumor size.

11 Claims, 2 Drawing Sheets

HIGH FREQUENCY THERMAL ABLATION OF CANCEROUS TUMORS AND FUNCTIONAL TARGETS WITH IMAGE DATA ASSISTANCE

"This application is a continuation of copending application(s) Ser. No. 08/167,676 filed on Dec. 15, 1993 now abandoned."

BACKGROUND TO THE INVENTION

The use of radiofrequency electrodes inserted into the body is well known for creating heat lesions, i.e. volumes of destruction of tissue. Heretofore, such lesions have been restricted to functional therapy or pain therapy, meaning that the electrode is inserted into neurological tissue or other tissue approximating nerves so as to heat the tissue by radiofrequency energy dissipation heating and thus to destroy a neurological structure that is the cause of a pain or motor problem. The literature has a large number of examples from many decades, and the equipment and applications are exemplified by the products of Radionics, Inc. in Burlington, Mass. Radionics makes radiofrequency generators (rf generators) and accessory rf electrodes for such therapeutic lesion generation. Recently, reports of use of Radionics equipment for destruction of tumors in the liver have been reported (Buscurini et al.). This involved insertion of an electrode made by Radionics with a hemispherical point and exposed conductive tip into tumors in the liver for the purpose of complete heating destruction by radiofrequency current (rf ablation) of a tumor. The electrode had a fixed tip length of about 10 millimeters and was inserted into the tumor under real time ultrasonic control. The electrode was placed within the tumor volume, and the rf heating done at an empirical level of temperature and radiofrequency generator voltage applied to the electrode. The temperature was measured by a temperature sensor installed within the tip of the rf electrode.

Tumors to be ablated may have great variability in their shape and size. They also can occur in or near critical structures such as the brain, where avoidance of the critical structures, both in terms of the entry tract of the electrode and in terms of the heating ablation zone, must be carefully considered. Heretofore, no method of using three-dimensional pre-planning has been done to implement tumor ablation with radiofrequency electrodes, nor has there been an attempt to select an appropriate tip length of the exposed rf electrode which is optimal to the approach direction and size of the tumor for that given probe tract. Thus, one of the objectives of the present invention is a method and associated apparatus to make such optimization possible.

Hyperthermia is a well known technique. This has typically been implemented by insertion of radiofrequency or microwave electrodes into a tumor volume so as to heat the tumor volume and sometimes nearby normal tissue to sub- or marginally lethal temperatures, and to combine such marginally lethal temperatures with doses of ionizing radiation. The combined effect of marginally elevated temperature and radiation is to selectively destroy tumor cells but spare normal cells, since the latter have the ability to withstand the heat and radiation process much better. This is the hyperthermia principle. It is radically different from the concept of heating a tumor volume to lethal temperatures over the entire tumor volume with the explicit purpose of simply killing all cells, usually without exception within the lethal or ablation isotherm volume. In the case of the present invention, we are describing an ablation volume, and not necessarily describing adjunct radiation therapy, as in the case of the hyperthermia principle. The use of adjunctive radiation therapy may be applied for other reasons in conjunction with the present invention, such as to treat outlying normal tissue that has not been substantially affected by the ablation process or to boost the kill process. The hyperthermia principle also makes use of fractionation or multiple exposures of heat and radiation to attempt to destroy the tumor cells during their cell cycle and spare the normal cells by the same cyclical cell division process. The present rf ablation technique deals typically with total destruction within the target tissue volume. Thus, there is a substantial difference between the hyperthermia method of the past and the present invention of interventive rf tumor ablation.

Part of the present invention is both method and apparatus for implementing the rf tumor ablation. Radionics, Inc. has a variety of electrodes that have been used for various functional or pain procedures, as mentioned above. These electrodes have had various shapes and structure. For example, the GSK Gildenberg Stereotactic Kit contains an electrode which has an insulated cannula and an uninsulated radiofrequency electrode that can be inserted within the cannula such that the length of exposure of the radiofrequency tip can be varied prior to insertion of the electrode or after insertion of the electrode into the body. Radionics also has the RRE Ray Rhizotomy Electrode, which has an insulated shaft, fixed exposed tip length, and a tip which has a sharpened trocar shape for self-penetration into the body.

The GSK Electrode is used for cingulum lesion destruction in the brain. The cingulum is known a priori to have typical dimensions, and thus the tip exposure may be set beforehand to correspond to general knowledge of the cingulum tip dimensions. However, never in the use of the GSK Electrode is it anticipated to do imaging studies of the anatomy to determine the size of a tumor or other target structure, and then set the tip exposure of the rf electrode to correspond to the dimension of the tumor from a given probe tract angle based on that imaging information. Thus, the intention of the GSK variable tip electrode was entirely different from the intention of the method in the present patent.

The sharp, trocar pointed RRE Electrode of Radionics was used for self-penetration of the tissue and placement of the electrode near the facet joints of the spine to cause heating of the neuro-musculature of the spine for pain relief. Nowhere was there ever the intention of using such a self-penetrating electrode for the treatment of cancerous tumors, nor was there any intention to devise a pointed electrode which has variable tip exposure to optimize the treatment of cancerous tumors. Thus, the method and design of the above-mentioned Radionics electrodes was distinctly different from that of the present invention. Another quantitative distinction between the GSK Electrode and the RRE Electrode with respect to the present invention is the size and length of the tips involved. Functional and pain lesions are typically never larger in dimension than approximately 10 mm in width and 10 to 14 mm in length. Thus, the tip exposure of the GSK variable tip electrode is limited to approximately 12 mm, and that of the RRE Electrode is limited to 7 mm. Furthermore, the diameter of these electrodes is 2 mm or less. With such limited tip sizes, limitation on lesion destruction volumes is reached. For the destruction of cancerous tumors, where the tumor volumes can be substantially greater than those just mentioned, much longer tip exposures would be required, and larger electrode tip diameters would also be required.

DESCRIPTION OF THE INVENTION

The present invention relates to insertion of one or more rf electrodes into a tumor (or other type of target structure) volume, where the tumor volume has been either predetermined or visualized by imaging techniques, so as to heat said tumor volume and destroy it substantially. A typical implementation of the present invention would be to scan the patient's anatomy by one or more of several scanning modalities, such as CT scanning, MRI scanning, ultrasound, PET scanning, etc., so as to visualize the tumor and the surrounding normal tissue. The tumor dimensions can thereby be determined, and the location of the tumor relative to critical structures and the external anatomy can be ascertained. By this means, the optimal approach of an electrode shaft into the body can be determined by the surgeon so as to minimize damage to intervening normal tissue and/or to achieve an optimal aspect to the tumor volume to be killed. As with stereotactic radiosurgery, which is planned on computer graphic workstations such as that offered by Radionics/RSA, the imaging data may be stored in the memory of the computer, and the tumor as well as normal anatomy rendered in graphic three dimensions or, alternatively, in two-dimensional slices. In this way, in the case of radiation surgery, i.e. so-called "radiosurgery," the surgeon can plan the optimal approaches and tumor volume prior to irradiating the body. A methodology involving radiofrequency electrodes is described in one implementation of the present invention. In the case of a brain tumor, where there are critical structures nearby, they may be avoided by the electrodes on the way in, and exact details of the tumor shape may be ascertained prior to electrode insertion so that the optimal electrode size can be selected and the optimal stereotactic approach of the electrodes may be made.

As one example of the invention, after pre-planning of the approach relative to the tumor, an optimal number and size of electrodes might be selected so that the ablation isotherms can optimally engulf and kill the tumor with a minimal number of electrode insertions and minimal damage to surrounding healthy tissue. In this process, an electrode of the appropriate width of unexposed heating tip and the appropriate length of exposed heating tip would be used.

Although the examples described here are for ablation of cancerous tumors, the inventions may equally well apply to other types of target volumes. For example, various types of benign tumors, neurological structures, or other tissue structures may also be ablated or heated for therapeutic reasons. They are intended to be included within the scope of this invention, and thus the term cancerous tumor may be replaced by tissue target volume throughout this description with equal relevance to the invention.

Figure 1:
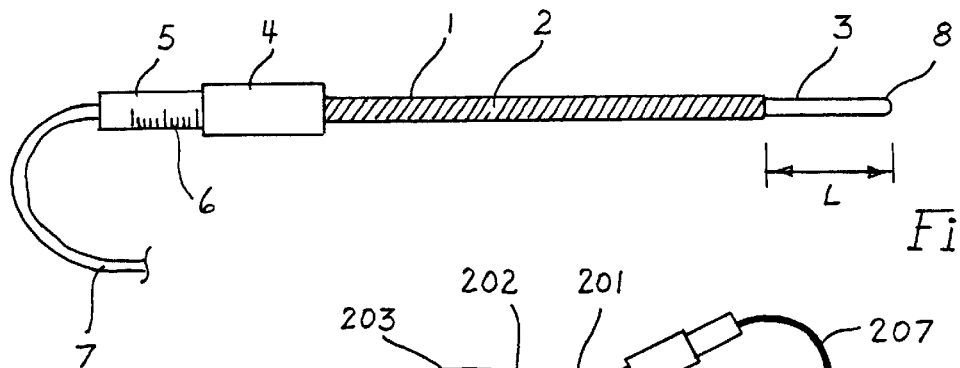
FIG. 1 shows an rf ablation electrode with variable tip length and hemispherical tip shape.

FIG. 1 shows such an rf heating electrode for ablation. It has a generally elongated shaft 1, which may be insulated over a portion of its surface 2. At its distal end, there is an exposed tip 3, which is electrically uninsulated. In this embodiment, it has a rounded, hemispherical tip 8. The tip length L may be varied by a variation of an uninsulated shaft 3, which can be inserted into the insulated shaft 1. The insulated shaft 1 has hub 4 fixed relative to it, and the uninsulated shaft 3 has hub 5 also connected to it respectively. By varying the relative insertion of hub 5 into hub 4, the surgeon can thereby change the degree of tip extension L of the rf or ablation tip at will. The degree of extension can be read out by scale means 6 at the electrode hubs. Connection means 7 may go to a radiofrequency generator apparatus outside of the body.

Figure 2:
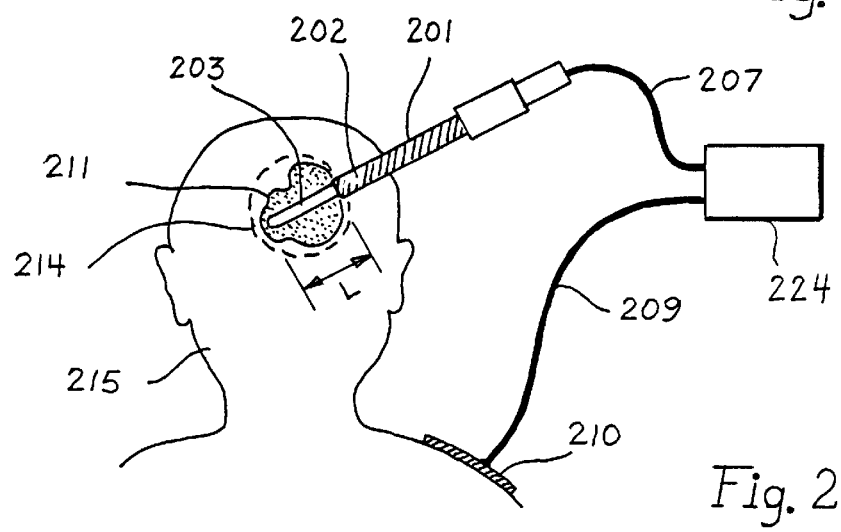
FIG. 2 shows the application of an rf ablation electrode in a tumor volume where the variable length of the tip exposure is tailored to the tumor dimension.

FIG. 2 shows a typical radiofrequency generator and electrode arrangement. Electrode 201, with its insulated shaft 202, is inserted into the body. The inner cannula 203 is shown with its exposed tip extending a length L beyond the insulated shaft 202. Connection cable 207 goes to the external radiofrequency generator 224. A reference connection 209 to the rf generator connects to a reference electrode 210, which has a relatively large area and supplies the return current from the rf generator when it passes through cable 207, the rf electrode tip 203, and the patient's body. The rf current flowing through this system heats the region around the electrode tip 203 to give heating zones or surfaces of constant temperature, referred to as isotherms. The isotherm of approximately 50° may be thought of as the ablation isotherm, since any tissue inside of that volume will be permanently killed. Such an ablation isotherm is schematically represented by the dashed line 214, which represents a surface around the exposed tip 203 and engulfing a cancerous tumor represented by the shaded volume 211.

In one embodiment, the method of the present invention would involve scanning the patient's body to visualize a cancerous tumor 211. One would visualize its shape and orientation relative to the patient's body 215. In this way, a judgment of the best approach of an rf electrode 201 and the dimension L of the tumor along the approach direction could be predetermined. This having been done, the electrode 201 could be inserted into the body 215, the electrode tip 203 with its appropriate length L could be placed properly within the tumor, the rf generator 224 could then create an rf voltage on the exposed electrode tip 203 so as to send rf current into the body and heat the tumor to a lethal temperature.

The exposed electrode tip 203 could have within it a temperature sensor which can measure the temperature of the heated zone within the tumor during the heating process. This can be implemented by temperature sensing connections through the cable 207 to the external apparatus, such as the rf generator, which may have various types of temperatures monitoring readouts. In this way, quantitative control of the heating process can be maintained.

In addition, real-time evaluation of the heating process can be carried out. For example, an ultrasonic detector used in conjugation and proximity to the rf electrode might be implemented so that the position of the electrode within the tumor can be seen in real time during or just prior to the lesion. This could be significant, since some tumors are firm, and one would wish to be sure that the rf electrode, once placed in the tumor, has not displaced the tumor and thereby made inaccurate the pre-imaging plan. Real-time CT and MRI imaging of the electrode within the tumor volume would also be a way of implementing such position monitoring. CT scanners are able to do two-dimensional stacks or in spiral patterns and thus volumetric scanning so as to visualize an electrode so implanted within the anatomy. Special electrode construction might be anticipated for this purpose with the electrode being made out of material that is not so radio-dense that it would cause inordinate artifact in such a CT scan. Electrodes such as titanium or a conductive composite could be considered for this purpose. Analogously, for real-time MRI monitoring of electrode placement prior to, during, or after the lesion process, rf electrodes which are MRI compatible should be considered. Electrodes made of high cobalt alloys such as nichrome, of platinum, or of titanium could be considered for this purpose. These concepts are claimed as part of the present invention.

The present invention is meant to include determination or selection of the appropriate electrode tip length(s) either by pre-scanning or by scanning during the operative procedure. As described above, pre-scanning would allow predetermination of the tip length(s) to cover the tip. However, interoperative scanning would enable the tip length(s) L to be adjusted real time to best cover the target volume.

As part of the pre-planning process, a computer graphic workstation could be used to not only render the anatomy and tumor pathology, but also enable visualization of one or more electrode tracts, the placement of the tip or tips within the tumor, and the ablation isotherms as they would occur during heating. For instance, there is empirical knowledge about the size and shape of rf heating isotherms within bodily tissue (Cosman et al.). Technical Aspects of RF Lesion Generation). This empirical knowledge or, alternatively, pre-calculated knowledge of spatial heating distributions could be used as part of the computer program which visualizes and pre-plans the rf ablation process. The theoretical, pre-planned isotherms might be rendered as surfaces in a variety of colors or transparency, superimposed upon the tumor and anatomical renderings in two dimensions or three-dimensional visualization in the computer graphic workstation. Optimization algorithms for placement of electrodes within a tumor volume and for electrode tip geometries and temperatures so as to optimally engulf the tumor with an ablation isotherm could be so implemented, also within the computer graphic workstation. Knowledge of tissue impedance and conductivities for various tissue species around the tumor volume or indeed for the tumor itself, depending on its nature and constitution, could be input into the computer planning code so as to do a spatial calculation of the thermal distribution expected for given rf lesion parameters, such as temperature and power, current, impedance, etc. These calculations are exemplified by finite element analysis calculations which involve power density inputs, tissue conductivities and impedances, blood flow, conduction and convection coefficients, and other physical parameters. These, too, could be part of the method of pre-planning the rf tumor ablation and displayed graphically or offered as menus and surgeon-manipulated or computer codes for pre-ablation planning.

The computer graphic workstation could be integral with the rf ablation generator such that it displays, real time, the lesion parameters such as temperature for each electrode, impedance, current, power, etc., as the lesion process proceeds. These parameters could be displayed graphically on the screen and tied visually to the graphics for full interactability as the process proceeds. For instance, graphical display of temperature for each electrode might be shown on a "window" within a field of the graphics display, which also includes graphic rendering of the electrode placement, axial, sagittal, or coronal views of the anatomy showing the tumor and the positioning of the electrodes, and isotherms as they grow as a function of the temperature, either theoretical or measured for each electrode tip. In this way, the maximum amount of information input would be available to the surgeon prior to, during, and after the lesion process. The rf ablation workstation concept, therefore, is part of the present invention and pulls together the lesioning process parameters and the parameters of the pathological and normal anatomy within one real-time, interactive visualization system.

Furthermore, stereotactic methods may be used to locate, calculate, and guide the electrodes into the region of the tumor. Stereotactic frames are well known for decades, and are exemplified by the apparatus sold by Radionics, Inc. This apparatus may hold and guide electrodes or other instruments in a direction and to achieve a target point. The target point may be calculated relative to a stereotactic patient attachment means, such as a head ring or frame or other patient securing system for immobilization. Graphic reference means such as a localizer structure with diagonal structures to provide indicia on tomographic slices may be used to locate and determine coordinates of anatomy and targets seen in the tomographic or volumetric image scans relative to the head rings, body holders, clamps, or external apparatus. Such methods are described in R. Brown's patents and papers as well as the brochures of Radionics, Inc. The stereotactic method is to direct the probe in a quantitative way to a point in space visualized by imaging methods, including plane films, CT, MRI, ultrasound, and other scanning methods. A quantitative or analog stereotactic holder system or frame could be used in conjugation with the rf ablation electrodes and the rf ablation generator and rf ablation workstation for this purpose. One or more electrodes could then be placed in a quantitative, pre-calculated way into the tumor volume for optimal ablation. The rf ablation computer workstation could store and display the stereotactic or imaging data in 2-D or 3-D representations, as well as simultaneous graphic renderings of the rf electrodes, targets, stereotactic guide, rf isotherms, etc.

Figure 3:
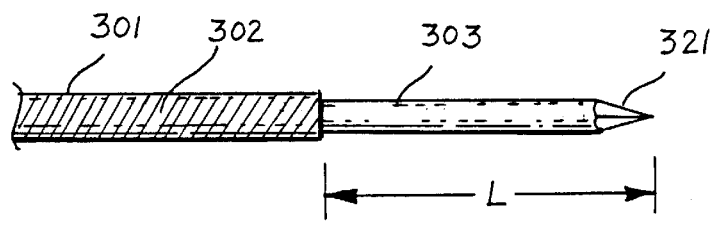
FIG. 3 shows a variable length rf ablation electrode with sharpened point for self-penetration of tissue.

FIG. 3 shows a further embodiment of the apparatus of the present invention. The electrode shaft 301 may be a metal cannula, and it may be insulated over its surface 302, indicated by the hatched area. Electrical current will not flow through the insulation, and thus heating of tissue will not occur near the insulated portion. The tip 303 may also be made of a metal tube such as stainless steel or other conductive metals, and it has a sharpened, trocar point 321. Its length L can be adjusted in the same way as the length adjustment shown in FIG. 1. In this situation, the exposed tip 303 may be the lesion tip and, because it is uninsulated, the rf current or microwave current will flow from it, heating the nearby tissue. Because the length is variable, the degree of lesion size may be tailored for the tumor margin limits. Because the point 321 is sharp, this electrode itself may be used to penetrate tough tissue such as the outer skin to go into areas such as the liver, prostate, musculature, etc. to reach the tumor and ablate it. Thus, this is a self-penetrating electrode for tumor ablation.

Figure 4:
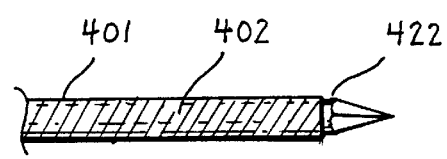
FIG. 4 shows the insulated cannula of an rf ablation electrode with a pointed stylet in place for penetration of tissue percutaneously.

An alternative instrument scheme of the invention may be illustrated in FIG. 4, in which again the cannula 401 is insulated over its surface 402 and there is a stylet, the tip of which is shown as 422, which has, in this case, a sharpened, trocar point. The cannula 401 may be inserted through tough tissue with the rugged stylet 422 in place. When the penetration is sufficient, the stylet 422 may be removed and a more hemispherically shaped rf electrode, such as that shown in FIG. 1 and represented by tip 3 with its rounded point 8, may be inserted into the cannula 401 to give a smooth, non-cutting presentation to the tumor volume. This may be especially important when there is vasculature which could be ruptured. Thus, a cannula with a sharpened stylet can be used in conjugation with an rf electrode as a set of instruments for penetration and for tumor ablation. This set concept is claimed also as part of the present invention.

Figure 5:
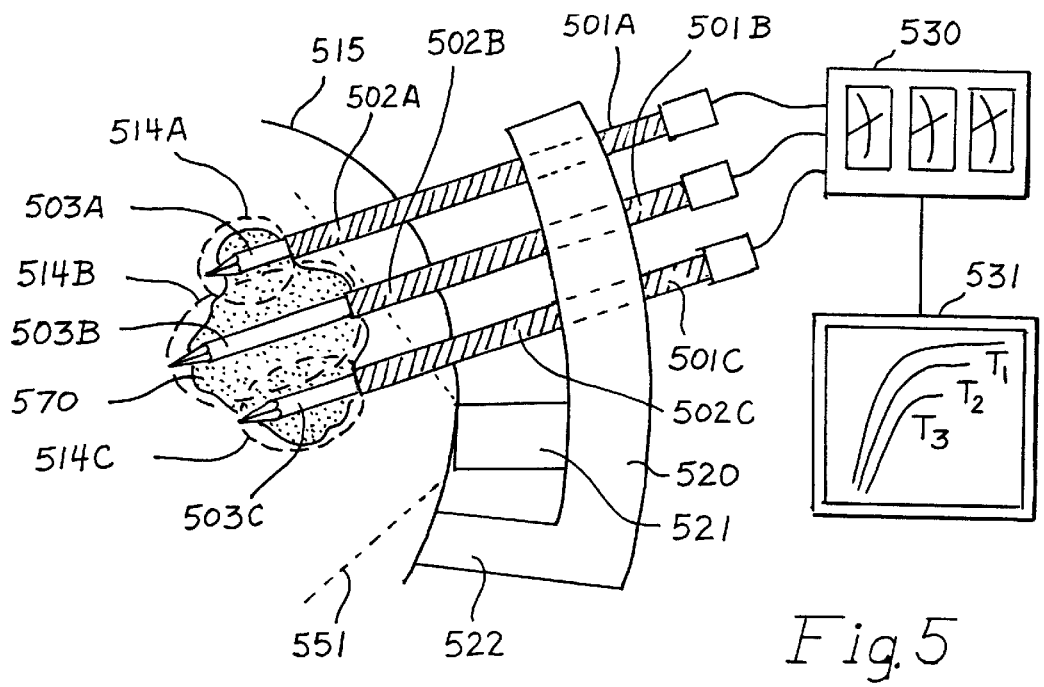
FIG. 5 shows the insertion of multiple rf ablation electrodes into a tumor volume to optimally envelop the tumor with ablation isotherms.

FIG. 5 shows the implementation of multiple electrodes guided stereotactically into a tumor volume and illustrates how the tumor volume may be enveloped by ablation isotherms with multiple electrodes. Electrodes 501A, 501B, and 501C are inserted stereotactically and guided by the frame 520 to a target volume, which is the tumor represented by the irregular region 570. The electrodes have their respective insulated shafts 502A, 502B, and 502C, which do not emit rf current and therefore do not heat tissue in their proximity. The uninsulated tips 503A, 503B, and 503C have differing lengths which are tailored to accommodate the size of the tumor for each of the electrode tracts. Thus, when the rf voltage is applied to the electrode, the rf current driven by that voltage will heat a region around each of the electrode tips, creating isotherms of different temperature around each tip. The dashed isotherms 514A, 514B, and 514C illustrate the ablation isotherm which may correspond to surfaces of constant temperature, approximately 50°. All tissue within those ablation isotherms will be permanently killed if the temperature is maintained for times on the order of 30 seconds or more. Thus, one can see from FIG. 5 that the ablation isotherm enveloped the tumor volume region 570, and, in this way, planning can be done for electrode placement and tip lengths to fully encompass and kill the tumor.

Each of the electrodes may be connected either in some time sequence or at the same time to an external apparatus 530, which would be for rf electrodes the rf lesion generator. It supplies the voltage sequentially, in parallel, or in various time sequences to the electrodes to implement the heating. Also shown in the instrument 530 are temperature meters which could read out the temperature from a temperature sensor installed in each of the electrodes' tips. In this way, quantitation and grading of the heating process can be carried out by the operator or by automatic controls in the lesion generator 530.

Also shown is a connection from the rf generator to graphic means such as a graphic computer workstation 531. This would provide the capability to monitor, chart out, and graphically display parameters associated with the ablation process such as, for example, the temperature $T_1$, $T_2$, and $T_3$, as registered on each one of the electrodes during the heating process. The time evolution of these temperatures, as illustrated in the graph in FIG. 5, would give the operator an immediate impression of the ablation process, and would lead to important safety controls and quantitation. Other parameters, such as power, impedance, current, voltage, etc., as well as lesion parameters, could be displayed on such a graphic display for increased monitoring of the process.

In FIG. 5 is also shown a schematic diagram of a stereotactic apparatus or guide 520. It may be attached in a variety of ways to the patient, but it is illustrated schematically as attachment means 522 to anchor it or otherwise immobilize it to the patient's body. In reality, this could be a head ring or a body cast or other clamping means to the body that will immobilize the stereotactic arc. The arc can accommodate parallel, multiple electrodes, as shown, and also may accommodate diagnostic scanning means such as element 521. This may be, for example, an ultrasonic scanner and may generate a fan of ultrasonic waves, illustrated by dashed lines 551, so as to scan the anatomy and visualize the electrodes as they are being placed into the tumor volume. This would give a real-time, interactive view of the placement of the electrodes to be sure they are in the proper location. In that regard, see U.S. Pat. No. 5,662,111 to Cosman, entitled "Process of Stereotactic Optical Navigation," entitled to a priority date of Jan. 28, 1991. An analogous scanner, which could be cooperatively coupled to a stereotactic frame and therefore to the electrodes and anatomy, would be a CT or MRI scanner installed in the operating theater or in the radiographic suite to monitor the process and implantation of the electrodes as well as the heating process directly at the time of heating. Thus, imaging techniques can be used prior to, before, and after ablation to further make this procedure safe and effective and confirm the placement of electrodes or even the course and effect of the ablation process itself.

Figure 6:
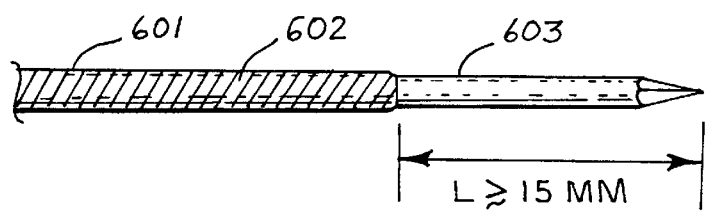
FIG. 6 shows a fixed length tip exposure for an rf ablation electrode, where said electrode has pointed tip for self-penetration of tissue.

FIG. 6 shows another implementation of an ablation electrode which has a fixed, uninsulated tip exposure with length L. The electrode may be a continuous metal shaft. The shaft 601 is an elongated structure with insulated portion 602, near which no heating will take place, and uninsulated portion 603, where the rf current will spread out and heat the tissue. This tip is similar to the RRE Kit of Radionics, in that it has a pointed trocar tip, however, one distinction relative to this invention is the general size of the rf electrodes here as opposed to previous applications. In previous applications, tip sizes almost never exceeded 10 to 12 mm. In the rf ablation application, tip sizes can easily exceed 15 mm and go on up to 20, 30, 40 mm or more in length. Tip diameters also will be considerably larger. RF electrode tips for functional and pain work will typically never exceed 2 to 2.5 mm. Lesion electrode diameters of 2.5 mm and greater would be commonplace for the rf ablation application. Thus, the rf ablation brings the electrodes into a new dimension in the domain of size which was not anticipated heretofore, and this should be considered part of the present invention.

Figure 7:
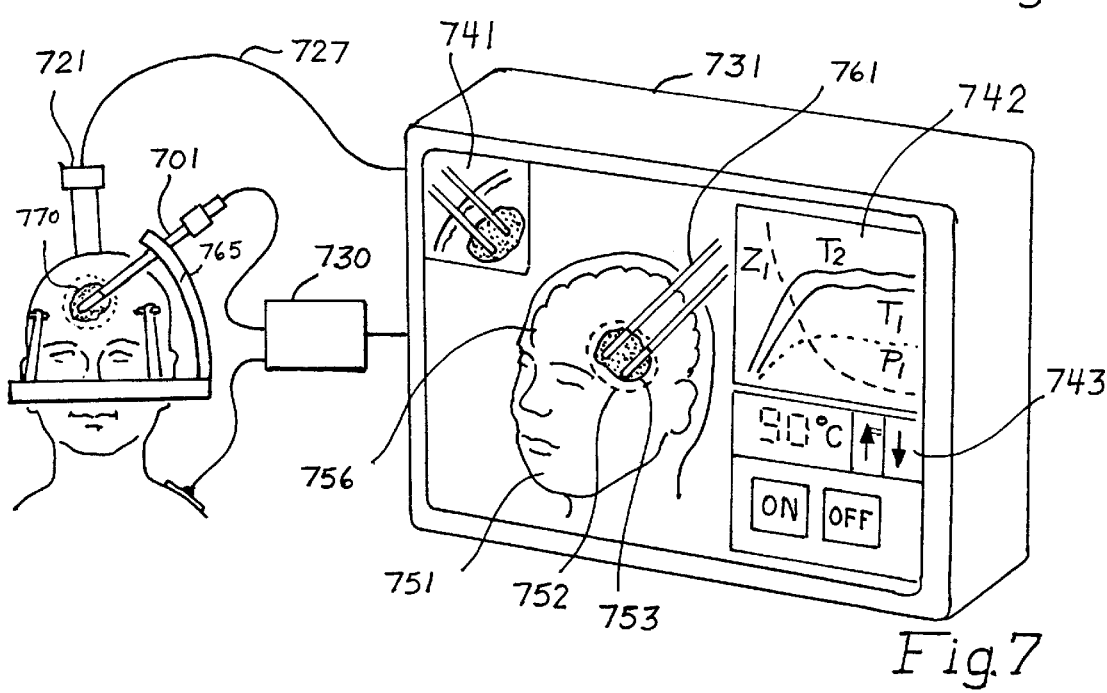
FIG. 7 shows the use of rf ablation electrodes in conjunction with a holding device such as a stereotactic apparatus and also in conjunction with a computer graphic display for visualization, planning, and control of the rf ablation process.

FIG. 7 shows an integrated approach to rf ablation consisting of an electrode system in cooperative conjugation with an external apparatus for supplying of heating power to the electrode, also in conjugation with a multi-modality computer graphic workstation. In this figure, electrode 701 is being held stereotactically by arc system 765. The tumor volume 770 is being ablated, and the process is being monitored by ultrasonic monitor 721. The electrode is connected to the rf generator 730. The rf generator in turn is coupled to a computer graphic workstation 731, as is the ultrasonic monitor 721 via cable 727. The computer graphic workstation and monitor keep track of multiple functions. Illustrated here is a 3-D graphic rendering 751 of the patient's head which would be derived, for example, from comprehensive two-dimensional or three-dimensional volumetric image data acquisition, as from a CT, MRI, ultrasonic, SPECT, or other scanning means. From such renderings, segmentation of skin, skull, and brain can be automatically or manually done. Here the brain coordinate 756 is rendered, as well as the external contour of the skin and face. Illustrated in the figure is the electrode(s) 761. This representation could be manipulated real time by the user on the computer screen and placed in an orientation with an optimal approach to the tumor target volume 753. Calculations or algorithms for the isotherm resulting from a given temperature can also be represented as a transparent surface, wire frame, or volumetric object such as the dashed region 752. In this way, the operator can predetermine from a placement of electrodes that the ablation isotherms will envelop the tumor. Also shown on the monitor are other displays with information of importance. For example, in the display window 742 are shown critical lesion parameters such as temperature, impedance, power, voltage, and current from each of the electrodes, all shown in a time progression, possibly in different colors so as to highlight the actual progress of the heating as it is being done. In addition, in window 743 are digital displays of temperature readout from the electrodes as well as icons shown with the up and down arrows, which may be manipulated by the surgeon so as to change the power level on the electrode or electrodes by means of a mouse or touch display. On and off functions, as well as other control or functionality features, could be placed within windows or buttons on the screen so that the entire process of ablation, both monitoring and control of the systems such as the lesion generator 730, may be manipulated and controlled interactively on the same computer graphic screen. Also shown in the window 741 is a graphic display from the scanner 721 of the actual lesion process as it is proceeding. The electrodes are rendered, and, in addition, the rendering of the anatomy and the tumor volume are seen in real time. In this way, the computer graphic predicted placement of electrodes 761 and their geometry such as tip length, curvature, direction of path, etc. into the graphic anatomy 751 can be confirmed in sectional or 3-D views by the representation of 741.

Thus, the present invention is meant to claim a computer graphic workstation which controls part of the entire function of the tumor ablation process. This could include without limitation the control and monitoring of the power levels to the rf ablation electrode or electrodes, the control of the generator functions, the display of the generator functions, manipulation of the displays with computer graphic icons or menus, the use in conjugation with all of the above functionalities of 3-D graphic displays of the anatomy, pathology, tumor volume, electrode positions as selected by the surgeon, and temperature isotherms as they would be represented relative to the tumor volume. All of this in one comprehensive control station would put at the fingertips of the neurosurgeon a realistic graphic display of all of the important parameters associated with the ablation process. No such computer graphic workstation has ever been developed for the purpose of radiofrequency heating and, in particular, for the process of radiofrequency heating for tumor ablation. This is then claimed for the present invention.

There are many variations of the embodiments shown within the present patent application which would be obvious to those skilled in the art, but still claimed under the scope of this invention. For example, many other geometries of electrodes, including straight, off-axis, and steerable electrodes, are intended to be included within the scope of this invention for tumor ablation. A variety of stereotactic holders and methods of target calculation, both frame-based and frameless, could be described. The method of heating of the probe could be either radiofrequency current, as illustrated here, or current in the microwave region, or, for that matter, direct heating of resistant elements within the electrode itself. Nichrome heaters in the electrodes, or even circulation of heated fluids within the electrodes, could achieve a similar effect as what has been mentioned in the examples above. CT and MR scanners may be of new and novel types involving spiral scanning, volumetric image acquisition, and high-speed imaging, and this may be included in the concept of CT or MR "tomographic" imaging used as illustrations in this invention description.

We could refer to the "target volume," target matter," or target structure," in this invention as tissue or tumor or any material in the body to be ablated. The present invention is meant to include ablation in any part of the body and in any tissue type, including without limitation, brain tissue, tumors, heart tissue, bone or bone tumors, spinal neural structures, intervertebral disks, muscle, and so on. For example, use of rf electrodes for cardiac ablation of aberrant tissue in the heart is now commonplace to cure certain cardiac arrhythmias and tachycardia. Scanner imaging of the heart is technically possible, and this data could be stored in a computer workstation to give the operator a 2-D or 3-D view of the cardiac anatomy to plan the rf ablation as described in this invention. The proper electrode size and the best approach to the cardiac target could be "seen" on the computer display. Lesion and recording parameters could also be developed to control and monitor the ablation process. Thus, the cardiac target application is a good example that is within the scope of this invention.

Having described, therefore, the embodiments of the present invention, what I claim by U.S. Letters Patent are the following:

1. A radio frequency heating process for the ablation of target tissue in the body of a patient, comprising the steps of:

storing image scanner data taken by volumetric image data acquisition from the body of the patient including the target tissue;

using said stored image scanner data to display a real time image of the body of the patient including the target tissue;

providing an elongated electrode structure with an insulating cover to define an exposed tip extending from said cover;

based on the displayed image of the body of the patient including the target tissue, inserting said elongated electrode structure into the body of the patient to position said tip contiguous to the target tissue; and based on the displayed image of the body of the patient including the target tissue, energizing said elongated electrode structure with radio frequency electrical energy to radiate energy from said tip for ablating the target tissue in the body of the patient.

2. A process in accordance with claim 1 wherein the step of providing an elongated electrode structure further includes the provision of at least one electrode with said exposed tip of at least 12 millimeters length and at least 2.5 millimeters diameter.

3. A process in accordance with claim 1 wherein the step of providing an elongated electrode structure includes providing a plurality of shafts defining a plurality of tips to be positioned contiguous to the target tissue.

4. A process in accordance with claim 1 wherein the step of providing an elongated electrode structure includes providing an electrode with a variable length exposed tip extending from said cover.

5. A process in accordance with claim 1 wherein said step of displaying an image comprises displaying a real time image of the body of the patient including the target tissue using the image scanner data to drive a computer graphics workstation.

6. A process in accordance with claim 5 wherein said step of displaying further includes displaying functions of ablating said target tissue in the body of the patient.

7. A process in accordance with claim 1 wherein said step of storing image scanner data comprises storing data from a CT, MRI, ultrasonic or SPEC scanning means.

8. A process in accordance with claim 1 further including a step of utilizing an ultrasonic monitor to monitor the ablating of the target tissue.

9. A process according to claim 1 further including a step of affixing a stereotactic arc system to the patient and affixing said elongated electrode structure to be held stereotactically by said stereotactic arc system.

10. A process according to claim 1 further including a step of monitoring critical lesion parameters attendant the ablation of the target tissue and displaying said critical lesion parameters with said displayed image of the body of the patient including the target tissue.

11. A process according to claim 1 wherein the step of providing an elongated electrode structure is partly based on the displayed image of the body of the patient including the volume of the target tissue.

\* \* \* \* \*